(12) United States Patent
Akashi et al.

(10) Patent No.: US 9,810,642 B2
(45) Date of Patent: Nov. 7, 2017

(54) TUNNEL LINING SURFACE INSPECTION SYSTEM AND VEHICLE USED IN TUNNEL LINING SURFACE INSPECTION SYSTEM

(71) Applicant: WEST NIPPON EXPRESSWAY ENGINEERING SHIKOKU COMPANY LIMITED, Takamatsu-shi, Kagawa (JP)

(72) Inventors: Yukio Akashi, Takamatsu (JP); Kazuaki Hashimoto, Takamatsu (JP); Shogo Hayashi, Takamatsu (JP)

(73) Assignee: WEST NIPPON EXPRESSWAY ENGINEERING SHIKOKU COMPANY LIMITED, Kagawa (JP)

( * ) Notice: Subject to any disclaimer, the term of this patent is extended or adjusted under 35 U.S.C. 154(b) by 3 days.

(21) Appl. No.: 14/904,740

(22) PCT Filed: Dec. 3, 2014

(86) PCT No.: PCT/JP2014/082022
§ 371 (c)(1),
(2) Date: Jan. 13, 2016

(87) PCT Pub. No.: WO2016/013133
PCT Pub. Date: Jan. 28, 2016

(65) Prior Publication Data
US 2016/0223471 A1    Aug. 4, 2016

(30) Foreign Application Priority Data

Jul. 25, 2014  (JP) .................................. 2014-152323

(51) Int. Cl.
*G06K 9/00*       (2006.01)
*G01N 21/954*  (2006.01)
(Continued)

(52) U.S. Cl.
CPC ........... *G01N 21/954* (2013.01); *G01B 11/25* (2013.01); *H04N 13/0242* (2013.01);
(Continued)

(58) Field of Classification Search
None
See application file for complete search history.

(56) References Cited

U.S. PATENT DOCUMENTS 9,110,170 B1 *  8/2015  Woollard ............... G01C 21/00
2006/0225293 A1 * 10/2006  Godwin .................. B60D 1/36
33/264
(Continued)

FOREIGN PATENT DOCUMENTS

JP   5-256633 A    10/1993
JP   2011-95222 A   5/2011
JP   2014-95627 A   5/2014

OTHER PUBLICATIONS

International Search Report for PCT/JP2014/082022 dated Jan. 20, 2015.

*Primary Examiner* — Tahmina Ansari
(74) *Attorney, Agent, or Firm* — Sughrue Mion, PLLC

(57) ABSTRACT

The tunnel lining surface inspection system capable of measuring the three dimensional shape of the surface of the tunnel lining surface to precisely determine whether cracking has a risk of leading to flaking, by the light section method using the photography means and the slit laser beam projecting means, mounted in the vehicle, while the vehicle is traveling in the tunnel, and the vehicle used in the system are proposed. Image processing is performed to obtain the image used for inspecting the tunnel lining surface, by using the result of the three dimensional shape measurement of one side face of the tunnel lining surface, measured while the photography means/slit laser beam projecting means arrangement means is fixed to the first measurement posi-
(Continued)

tion, and the result of the three dimensional shape measurement of the other side face of the tunnel lining surface, measured while the photography means/slit laser beam projecting means arrangement means is fixed to the second measurement position.

4 Claims, 8 Drawing Sheets

(51) Int. Cl.
  *G01B 11/25* (2006.01)
  *H04N 13/02* (2006.01)
(52) U.S. Cl.
  CPC . *H04N 13/0253* (2013.01); *G01N 2021/9548* (2013.01); *G01N 2201/0216* (2013.01); *G01N 2201/06113* (2013.01); *G01N 2201/12* (2013.01)

(56) References Cited

U.S. PATENT DOCUMENTS

| | | | |
|---|---|---|---|
| 2010/0259361 A1* | 10/2010 | Al Shahrani | E01F 13/126 340/5.71 |
| 2013/0191070 A1* | 7/2013 | Kainer | B61K 9/08 702/167 |
| 2016/0223471 A1* | 8/2016 | Akashi | G01N 21/954 |
| 2016/0227126 A1* | 8/2016 | Akashi | G01N 21/954 |

* cited by examiner

10(10a,10b,10c,10d,10e,10f)
20(20a,20b,20c,20d,20e,20f)

(a)

(b)                (c)

TUNNEL LINING SURFACE INSPECTION SYSTEM AND VEHICLE USED IN TUNNEL LINING SURFACE INSPECTION SYSTEM

TECHNICAL FIELD

The present invention relates to the tunnel lining surface inspection system and the vehicle used in the tunnel lining surface inspection system, in particular to the system and the vehicle for inspecting the soundness (degree of deterioration) of a tunnel by obtaining the image indicating the three dimensional shape including the height information of the tunnel lining surface.

BACKGROUND ARTS

The applicant already proposed the travel road surface inspection system in which, while a vehicle is traveling, the three dimensional shape (traverse direction, longitudinal direction, height) of the surface of the travel road surface is measured by the light section method using the photography means and the slit laser beam projecting means, mounted in the vehicle, as shown in the Patent document 1.

According to the invention proposed in the Patent document 1, the image indicating the three dimensional shape of the travel road surface can be obtained while a vehicle is traveling, and, by using the image, the soundness (degree of deterioration) of the travel road surface can be inspected by being capable of precisely confirming the unevenness such as a wheel track generated on the travel road surface.

the Patent document 1: Japanese Patent Application Laid-open No. 2014-95627

DISCLOSURE OF INVENTION

Problems to be Solved by the Invention

When cracking on the tunnel lining surface is photographied on the visualized image with merely two dimensional information without height information, it is impossible to determine whether the cracking has a risk of leading to flaking.

The present invention has been made by taking such actual states into account, and is aiming at proposing the tunnel lining surface inspection system capable of measuring the three dimensional shape of the surface of the tunnel lining surface to precisely determine whether cracking has a risk of leading to flaking, by the light section method using the photography means and the slit laser beam projecting means, mounted in the vehicle, while the vehicle is traveling in the tunnel, and the vehicle used in the system.

The first invention is characterized with a tunnel lining surface inspection system wherein, while a vehicle is traveling in a tunnel, a three dimensional shape of a surface of a tunnel lining surface is inspected by using a light section method using photography means and slit laser beam projecting means mounted in the vehicle, and is processed into an image used for inspecting the tunnel lining surface, the system comprising photography means/slit laser beam projecting means arrangement means having an arc surface shaped or approximately arc surface shaped arrangement surface corresponding to one side face in both side faces of the tunnel lining surface and being installed in the vehicle, wherein a plurality of slit laser beam projecting means for projecting a long slit laser beam along a circumferential direction of the tunnel lining surface to each area along a circumferential direction of the one side face in the both side faces of the tunnel lining surface are arranged along the circumferential direction of the arc surface shaped or approximately arc surface shaped arrangement surface, and a plurality of photography means for photographing from a direction different from a projecting direction of the plurality of slit laser lights the each area along the circumferential direction of the one side face in the both side faces of the tunnel lining surface are arranged corresponding to the each of the plurality of slit laser beam projecting means, along the circumferential direction of the arc surface shaped or approximately arc surface shaped arrangement surface, apart from a position where the slit laser beam positioning means are arranged by a predetermined distance in a vehicle traveling direction, fixing/reversing means for fixing the photography means/slit laser beam projecting means arrangement means to a first measurement position where a three dimensional shape of the one side face in the both side faces of the tunnel lining surface can be measured, and 180° reversing the photography means/slit laser beam projecting means arrangement means around a vertical center axis to fix the photography means/slit laser beam projecting means arrangement means to a second measurement position where the three dimensional shape of the other side face in the both side faces of the tunnel lining surface can be measured, and image processing means for performing image processing to obtain the image used for inspecting the tunnel lining surface, by using a result of the three dimensional shape measurement of the one side face of the tunnel lining surface, measured in a state where the photography means/slit laser beam projecting means arrangement means is fixed to the first measurement position and a result of the three dimensional shape measurement of the other side face of the tunnel lining surface, measured in a state where the photography means/slit laser beam projecting means arrangement means is fixed to the second measurement position.

The second invention is characterized, in the first invention, with a vehicle used in a tunnel lining surface inspection system wherein, while a vehicle is traveling in a tunnel, a three dimensional shape of a surface of a tunnel lining surface is inspected by using a light section method using photography means and slit laser beam projecting means mounted in the vehicle, and is processed into an image used for inspecting the tunnel lining surface, the system comprising photography means/slit laser beam projecting means arrangement means having an arc surface shaped or approximately arc surface shaped arrangement surface corresponding to one side face in both side faces of the tunnel lining surface and being installed in the vehicle, wherein a plurality of slit laser beam projecting means for projecting a long slit laser beam along a circumferential direction of the tunnel lining surface to each area along a circumferential direction of the one side face in the both side faces of the tunnel lining surface are arranged along the circumferential direction of the arc surface shaped or approximately arc surface shaped arrangement surface, and a plurality of photography means for photographing from a direction different from a projecting direction of the plurality of slit laser lights the each area along the circumferential direction of the one side face in the both side faces of the tunnel lining surface are arranged corresponding to the each of the plurality of slit laser beam projecting means, along the circumferential direction of the arc surface shaped or approximately arc surface shaped arrangement surface, apart from a position where the slit laser beam positioning means are arranged by a predetermined distance in a vehicle traveling direction, and fixing/reversing means for fixing the photography means/slit laser beam projecting means arrangement means to a first measurement position where a three dimensional shape of the one side face in the both side faces of the tunnel lining surface can be measured, and 180° reversing the photography means/slit laser beam projecting means arrangement means around a vertical center axis to fix the photography means/slit laser beam projecting means arrangement means to a second measurement position where the three dimensional shape of the other side face in the both side faces of the tunnel lining surface can be measured.

The third invention is characterized, in the first invention, with the tunnel lining surface inspection system, wherein the plurality of slit laser beam projecting means and the plurality of photography means are characterized in that they are arranged in zigzag along the circumferential direction of the arc surface shaped or approximately arc surface shaped arrangement surface.

The fourth invention is characterized, in the second invention, with the vehicle used in the tunnel lining surface inspection system, wherein the plurality of slit laser beam projecting means and the plurality of photography means are characterized in that they are arranged in zigzag along the circumferential direction of the arc surface shaped or approximately arc surface shaped arrangement surface.

Effect of the Invention

The present invention enables the three dimensional shape of the surface of the tunnel lining surface including the height information to be measured to precisely determine whether cracking has a risk of leading to flaking, by the light section method using the photography means and the slit laser beam projecting means, mounted in the vehicle, while the vehicle is traveling in the tunnel.

DESCRIPTION OF THE REFERENCE NUMERALS

Figure 1:
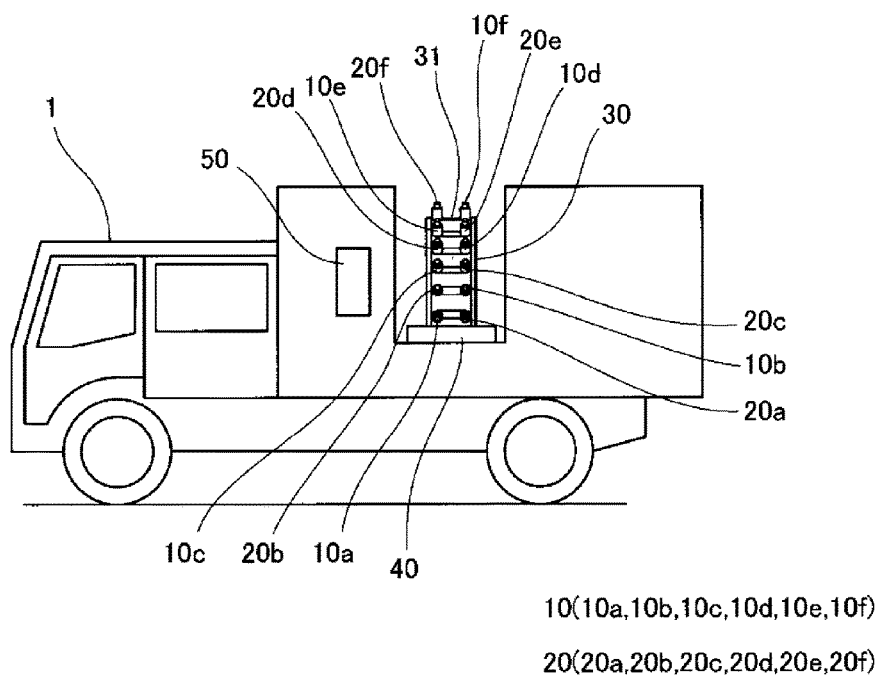
FIG. 1 shows the left side face of the vehicle used in the tunnel lining surface inspection system in the present invention.

1 Vehicle 10 (10a-10f) Photography means
20 (20a-20f) Slit laser beam projecting means
30 Photography means/slit laser beam projecting means arrangement means
31 Arc surface shaped or approximately arc surface shaped arrangement surface
40 Fixing/reversing means 41 Drive axis 100 Tunnel lining surface
100A-100L Each area

BEST EMBODIMENTS FOR IMPLEMENTING THE INVENTION

The embodiment of the tunnel lining surface inspection system and the vehicle used in the tunnel lining surface inspection system in the present invention is explained below while referring to the drawings.

DESCRIPTION OF THE REFERENCE NUMERALS

FIG. 1 shows the left side face of the vehicle 1 used in the tunnel lining surface inspection system in the present invention.

The vehicle 1 is a work vehicle with a base of work track used for road maintenance work, for example.

The loading space of the vehicle 1 has a container shape, and the door of one side face of the container (the left side face in FIG. 1) and the door of the ceiling of the container are openable. FIG. 1 shows the state where the doors are opened.

The photography means 10 (10a, 10b, 10c, 10d, 10e, 10f) and the slit laser beam projecting means 20 (20a, 20b, 20c, 20d, 20e, 20f) are arranged in the loading space of the vehicle 1 so that, when the above doors of the vehicle 1 are opened, the tunnel lining surface can be photographied and illuminated. The photography means 10 and the slit laser beam projecting means 20 are arranged in the photography means/slit laser beam projecting means arrangement means 30. The photography means/slit laser beam projecting means arrangement means 30 comprises the arc surface shaped or approximately arc surface shaped arrangement surface 31. The plurality (six) of slit laser beam projecting means 20a, 20b, 20c, 20d, 20e, 20f and the plurality (six) of photography means 10a, 10b, 10c, 10d, 10e, 10f are arranged in zigzag along the circumferential direction of the arc surface shaped or approximately arc surface shaped arrangement surface 31. The image processing unit 50 receives the image data photographied by the photography means 10 and performs image processing to generate three dimensional images of the tunnel lining surface.

Figure 2:
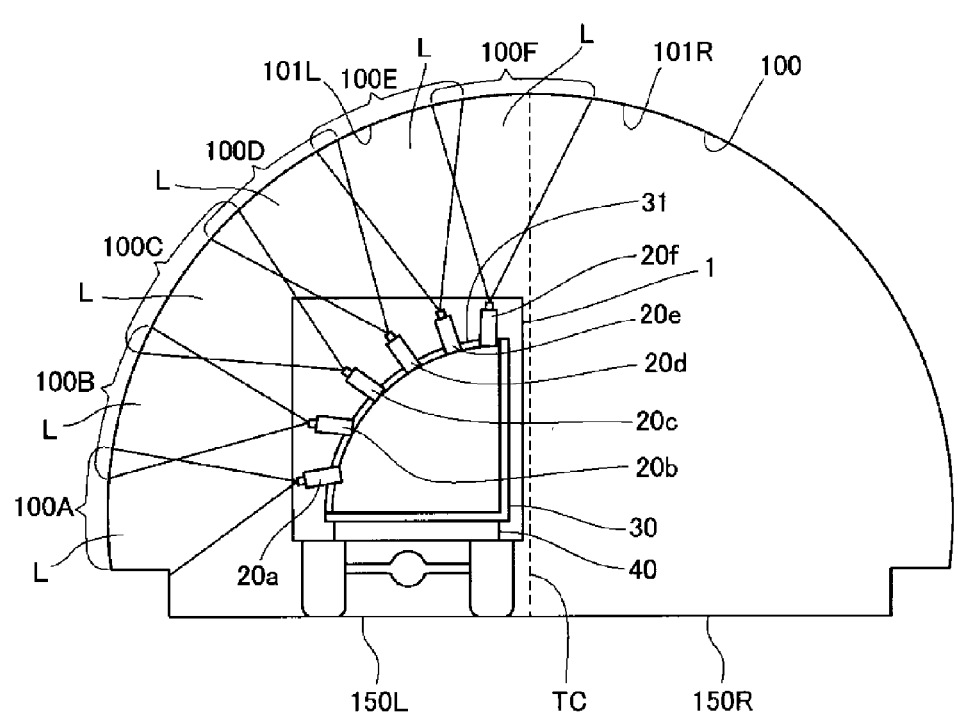
FIG. 2 is a cross section plan showing the state where the vehicle is traveling on the traveling lane on the left side in the tunnel and shows how the light section method using the photography means and the slit laser beam projecting means, mounted in the vehicle, measures the three dimensional shape of the surface of the tunnel lining surface.

FIG. 2 is a cross section plan showing the state where the vehicle 1 is traveling on the traveling lane 150L on the left side in the tunnel and shows how the light section method using the photography means 10 and the slit laser beam projecting means 20, mounted in the vehicle 1, measures the three dimensional shape of the surface of the tunnel lining surface 100. For convenience safe of explanation, the road surface on the left side of the center line TCU in the tunnel in the drawing is defined as the traveling lane on the left 150L, and the road surface on the right side of the center line TC in the tunnel in the drawing is dubbed as the overtaking lane on the right 150R. Also, the left side of the tunnel lining surface 100, delimited by the center line TC of the tunnel is defined as the left side face 101L, and the right side of the tunnel lining surface 100, delimited by the center line TC of the tunnel is defined as the right side face 101R.

The illumination means 20 is configured to comprise a plurality (six in the embodiment) of slit laser beam projecting means 20a, 20b, 20c, 20d, 20e, 20f projecting the long slit laser beam L along the circumferential direction of the tunnel lining surface 100 to each area of 100A, 100B, 100C, 100D, 100E, 100F along the circumferential direction of the left side face 101L, namely one side face in both side faces of the tunnel lining surface 100. It should be noted that, when the six slit laser beam projecting means 20a-20f are comprehensively described, they are dubbed slit laser beam projecting means 20, hereinafter.

The photography means 10 (not shown in FIG. 2, see FIG. 1) are line cameras, and configured to comprise a plurality (six in the embodiment) of photography means 10a, 10b, 10c, 10d, 10e, 10f photographing from the direction different from the projecting direction of the slit laser light L each area of 100A, 100B, 100C, 100D, 100E, 100F along the circumferential direction of the left side face 101L, namely one side face in both side faces of the tunnel lining surface 100. It should be noted that, when the six photography means 10a-10f are comprehensively described, they are dubbed photography means 10, hereinafter.

The slit laser beam projecting means 20 and the photography means 10 are arranged in the photography means/slit laser beam projecting means arrangement means 30 having the arc surface shaped or approximately arc surface shaped arrangement surface 31 corresponding to one side face in both side faces 101L, 101R of the tunnel lining surface 100.

Figure 3:
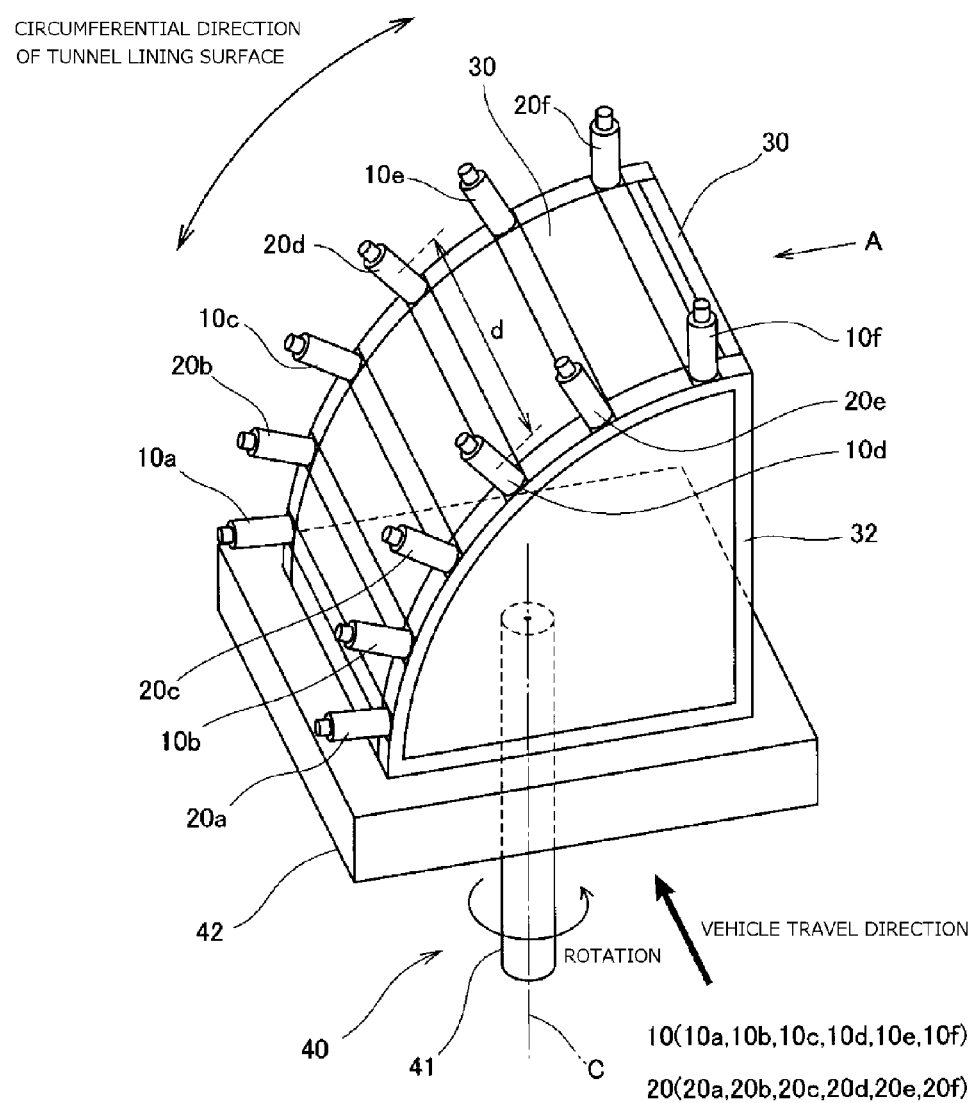
FIG. 3 is an oblique drawing showing the photography means/slit laser beam projecting means arrangement means.

FIG. 3 is an oblique drawing showing the photography means/slit laser beam projecting means arrangement means 30.

The six photography means 10a-10f are arranged respectively corresponding to each of the six slit laser beam projecting means 20a-20f, along the circumferential direction of the arc surface shaped or approximately arc surface shaped arrangement surface 31, apart from the position where the slit laser beam positioning means 20 are arranged by the predetermined distance d in the vehicle traveling direction.

To be more specific, the photography means/slit laser beam projecting means arrangement means 30 is configured to comprise the member 32 obtained by forming a cross section parallel to the circumferential direction of the tunnel lining surface 100, namely perpendicular to the traveling direction of the vehicle 1, into fan shape, and a pair of slit laser beam projecting means 20 and photography means 10 are arranged in the arrangement surface 31 corresponding to the arc surface shaped or approximately arc surface shaped surface of the fan-shaped member 32 at even or approximately even intervals along the circumferential direction.

Here, the plurality (six) of slit laser beam projecting means 20a, 20b, 20c, 20d, 20e, 20f and the plurality (six) of photography means 10a, 10b, 10c, 10d, 10e, 10f are arranged in zigzag along the circumferential direction of the arc surface shaped or approximately arc surface shaped arrangement surface 31.

Thereby, the neighboring slit laser beams L projected from each of the slit laser beam projecting means 20a, 20b, 20c, 20d, 20e, 20f and emitted to the each area of 100A, 100B, 100C, 100D, 100E, 100F can be prevented from being overlapped each other (see FIG. 2). Accordingly, the device can be easily set without any need of considering the interference of the silt laser beam L.

The fixing/reversing means 40 is configured to comprise the drive axis 41 which is the vertical center axis C of the photography means/slit laser beam projecting means arrangement means 30 and the stage 42. The stage 42 is fixed to the frame of the vehicle 1. The fixing/reversing means 40 fixes the photography means/slit laser beam projecting means arrangement means 30 to the first measurement position where the three dimensional shape of the left side face 101L, namely one side face in both side faces 101L, 101R of the tunnel lining surface 100 can be measured, and rotatably drives the drive axis 41 by a motor, etc. relatively to the stage 42 to 180° reverse the photography means/slit laser beam projecting means arrangement means 30 around the vertical center axis C, and fixes the photography means/slit laser beam projecting means arrangement means 30 to the second measurement position where the three dimensional shape of the right side face 101R, namely the other side face in both side faces 101L, 101R of the tunnel lining surface 100 can be measured.

FIGS. 2, 3 show the state where the photography means/slit laser beam projecting means arrangement means 30 is fixed to the first measurement position.

Figure 4:
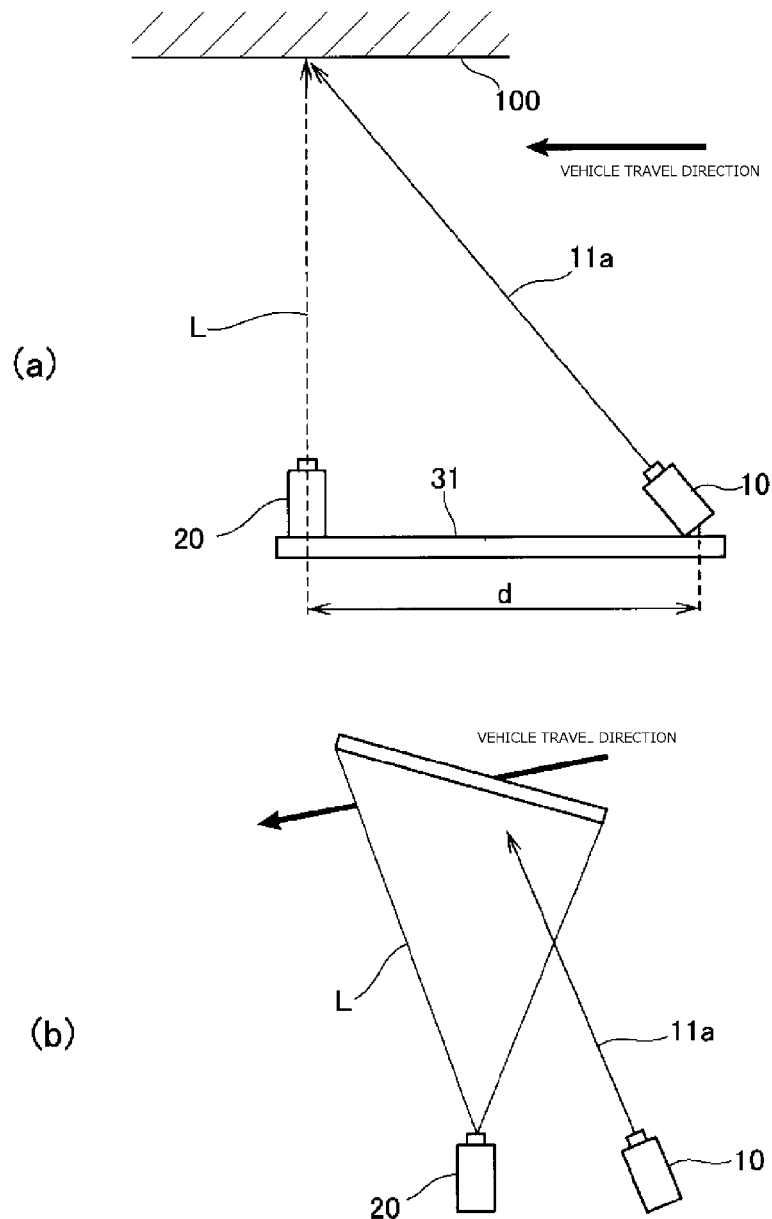
FIG. 4 shows how the projecting direction of the slit laser beam projected from the slit laser beam projecting means and the photography direction (collimation line) of the photography means are related to each other, FIG. 4(a) being seen from the arrow guiding A direction in FIG. 3, namely from the right side face of the vehicle, and FIG. 4(b) being an oblique drawing.

FIG. 4 shows how the projecting direction of the slit laser beam L projected from the slit laser beam projecting means 20 and the photography direction (collimation line 11a) of the photography means 10 are related to each other, FIG. 4(*a*) being seen from the arrow guiding A direction in FIG. 3, namely from the right side face of the vehicle 1, and FIG. 4(*b*) being an oblique drawing.

The slit laser beam projecting means 20 projects the slit laser beam L to the direction vertical to the surface of the tunnel lining surface 100, and emits the long slit laser beam L along the circumferential direction of the tunnel lining surface 100, namely the direction vertical to the traveling direction of the vehicle 1. The photography means 10 photographies the slit laser beam L emitted to the surface of the tunnel lining surface 100 from the oblique direction having the collimation line 11a inclined to the surface of the tunnel lining surface 100.

When the surface of the tunnel lining surface 100 is flat, the slit laser beam L emitted to the surface is photographied as a linear line. However, when the surface of the tunnel lining surface 100 is distorted from the unevenness, etc. of the surface, the slit laser beam L emitted to the surface is photographied as a distorted line. By profiling the distortion, the shape change of the surface of the tunnel lining surface 100 can be measured with the resolution of 0.5 mm or smaller.

Figure 5:
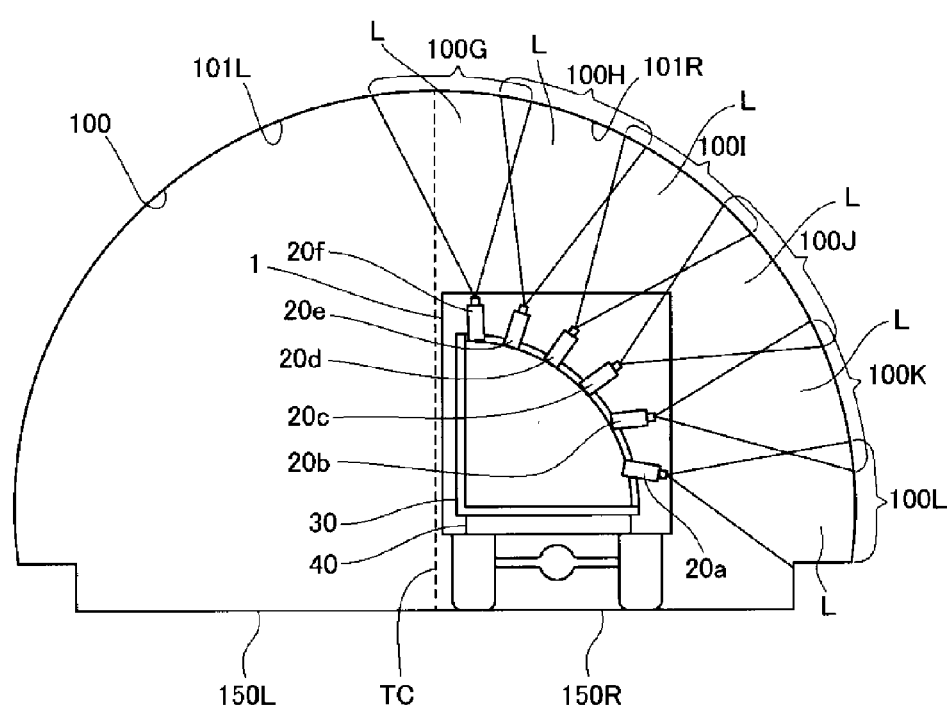
FIG. 5 is a cross section plan showing the state where the vehicle is traveling on the traveling lane on the right side in the tunnel.

FIG. 5 is a cross section plan showing the state where the vehicle 1 is traveling on the traveling lane 150R on the right side in the tunnel. FIG. 5 shows the state where the photography means/slit laser beam projecting means arrangement means 30 is 180° reversed around the vertical center axis C by the fixing/reversing means 40 from the first photography position and fixed to the second measurement position.

The slit laser beam projecting means 20f, 20e, 20d, 20c, 20b, 20a respectively project the long slit laser beam L along the circumferential direction of the tunnel lining surface 100 to each area of 100G, 100H, 100I, 100J, 100K, 100L along the circumferential direction of the right side face 101R, namely the other side face in both side faces of the tunnel lining surface 100.

The photography means 10f, 10e, 10d, 10c, 10b, 10a (not shown in FIG. 2) respectively photography from the direction different from the projecting direction of the slit laser light L each area of 100G 100H, 100I, 100J, 100K, 100L along the circumferential direction of the right side face 101R, namely the other side face in both side faces of the tunnel lining surface 100.

Here, as mentioned above, the plurality (six) of slit laser beam projecting means 20a, 20b, 20c, 20d, 20e, 20f and the plurality (six) of photography means 10a, 10b, 10c, 10d, 10e, 10f are arranged in zigzag along the circumferential direction of the arc surface shaped or approximately arc surface shaped arrangement surface 31 (see FIG. 3).

Thereby, the neighboring slit laser beams L projected from each of the slit laser beam projecting means 20f, 20e, 20d, 20c, 20b, 20a and emitted to the each area of 100G, 100H, 100I, 100J, 100K, 100L can be prevented from being overlapped each other.

Figure 6:
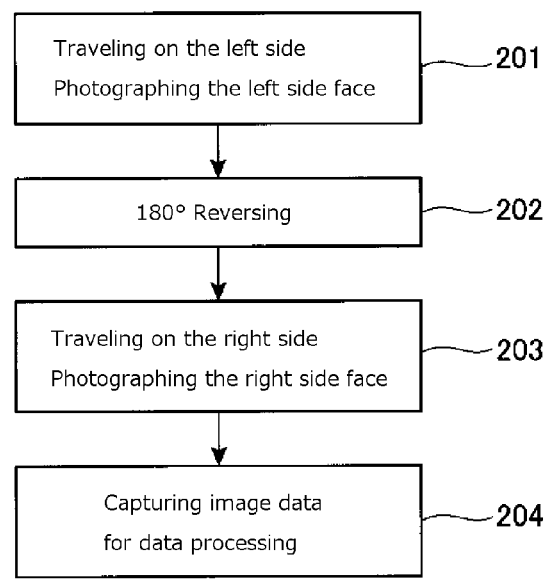
FIG. 6 shows a procedure of the processing performed in the tunnel lining surface inspection system in the embodiment.

FIG. 6 shows the procedure of the processing performed in the tunnel lining surface inspection system in the embodiment.

At first, while the photography means 10 and the slit laser beam projecting means 20 are fixed to the first measurement position, the vehicle 1 drives along the traveling lane 150L on the left side. While the vehicle 1 is traveling, the six photography means 10a-10f and the slit laser beam projecting means 20a-20f are activated. Thereby, each slit laser beam L emitted to each area 100A, 100B, 100C, 100D, 100E, 100F of the left side face 101L of the tunnel lining surface 100 is sequentially photographied by the six photography means 10a, 10b, 10c, 10d, 10e, 10f, as the vehicle 1 travels. The image data of the each area 100A-100F of the left side face 101L of the tunnel lining surface 100 photographied by the each photography means 10a-10f are captured into the image processing unit 50 (see FIG. 2; Step 201).

Then, the fixing/reversing means 40 180° reverses the photography means/slit laser beam projecting means arrangement means 30 around the vertical center axis C and fixes the photography means 10a-10f and the slit laser beam projecting means 20a-20f to the second measurement position (Step 202).

While the photography means 10a-10f and the slit laser beam projecting means 20a-20f are fixed to the second measurement position, the vehicle 1 travels along the overtaking lane 150R on the right side.

While the vehicle 1 is traveling, the six photography means 10a-10f and the slit laser beam projecting means 20a-20f are activated. Thereby, each slit laser beam L emitted to each area 100G, 100H, 100I, 100J, 100K, 100L of the right side face 101R of the tunnel lining surface 100 is sequentially photographied by the six photography means 10f, 10e, 10d, 10c, 10b, 10a, as the vehicle 1 travels. The image data of the each area 100L-100G of the right side face 101R of the tunnel lining surface 100 photographied by the each photography means 10f-10a are captured into the image processing unit 50 (see FIG. 5; Step 203).

The image data of the each area 100A-100F of the left side face 101L of the tunnel lining surface 100 and the image data of the each area 100G-100L of the right side face 101R of the tunnel lining surface 100, captured into the image processing unit 50 are captured into the exterior personal computer, for example, for image processing (Step 204).

Figure 7:
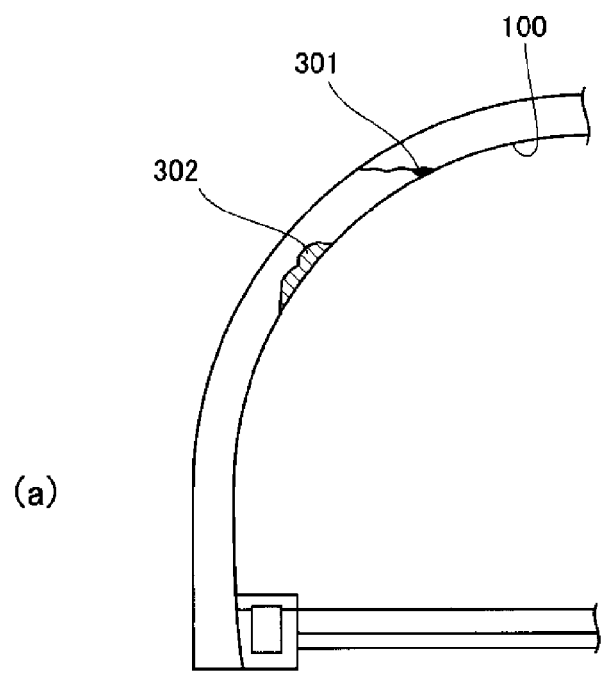
FIG. 7(a) shows the cracking formed on the construction joint of the tunnel lining surface and the cracking formed on a location other than the construction joint, in FIG. 7(b), the cracking formed on the construction joint of the tunnel lining surface is magnified, and in FIG. 7(c), the cracking formed on a location other than the construction joint of the tunnel lining surface is magnified.
Figure 7:
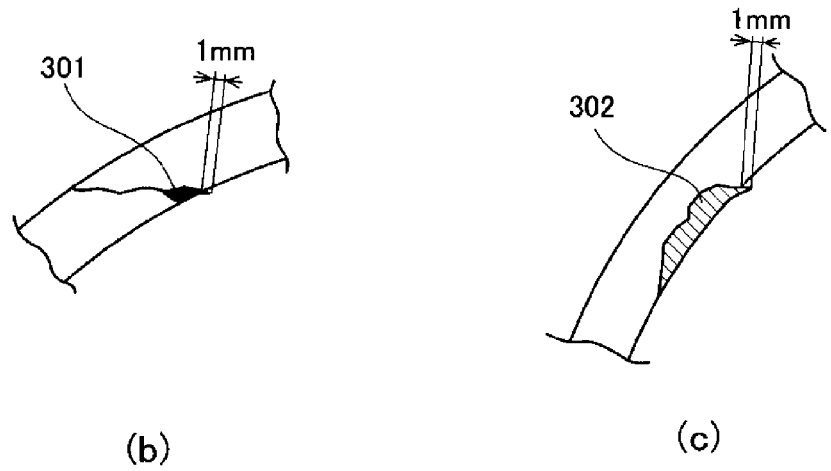

FIG. 7(a) shows the portion of the cracking 301 formed on the construction joint of the tunnel lining surface 100 and the portion of the cracking 302 formed on a location other than the construction joint.

In FIG. 7(b), the portion of the cracking 301 formed on the construction joint of the tunnel lining surface 100 is magnified. In FIG. 7(c), the portion of the cracking 302 formed on a location other than the construction joint of the tunnel lining surface 100 is magnified. In both cases, it can be identified that the uplift of around 1 mm is formed on the surface of the cracking 301, 302.

The construction joint has weak strength, and easily generates cracking. Merely by the use of visualized images, it is impossible to determine whether or not cracking generated on the tunnel lining surface 100 is the cracking which has uplift of no shorter than 1 mm which leads to flaking.

In the embodiment, the three dimensional shape image of the tunnel lining surface 100 is obtained, and thereby, it is possible to determine whether or not cracking generated on the tunnel lining surface 100 is the cracking which has uplift of no shorter than 1 mm which leads to flaking.

Figure 8:
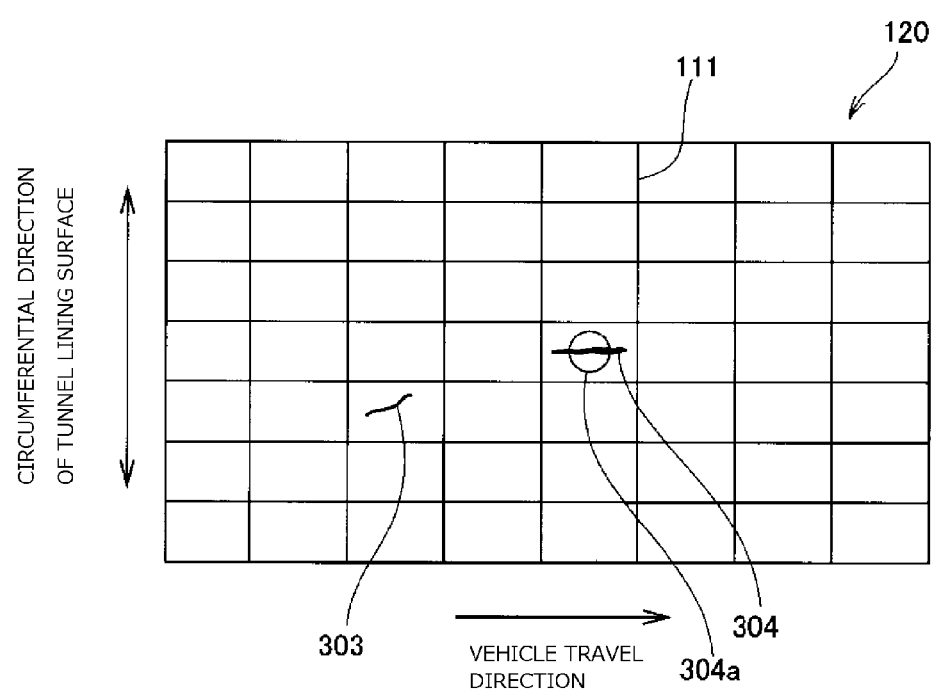
FIG. 8 shows an example of image processing performed in the personal computer.

FIG. 8 shows an example of image processing performed in the personal computer.

The three dimensional image 120 of the tunnel lining surface 100 in the region where the vehicle 1 traveled can be obtained for the entire circumference (left/right, both side faces 101L, 101R) of the tunnel lining surface 100 by connecting the image data of the each area 100A-100F of the left side face 101L of the tunnel lining surface 100 and the image data of the each area 100L-100G of the right side face 101R of the tunnel lining surface 100. In FIG. 8, "111" represents the joint delimiting each span of the tunnel lining surface 100.

The three dimensional image 120 is the height image showing the height of the tunnel lining surface 100 according to each two dimensional position in the circumferential direction of the tunnel lining surface 100 and the traveling direction of the vehicle 1. For example, the color of the higher portions changes into the brighter and the color of the lower portions changes into the darker.

For example, when the cracking 303 on the three dimensional image 120 is displayed lighter, and the cracking 304 on the three dimensional image 120 is displayed darker, it can be identified that the cracking 304 has larger uplift and thus, has higher risk of flaking. Conventionally, the visualized image with no height information has failed to eliminate the possibility of erroneously identifying the color unevenness or stain formed on the tunnel lining surface 100 as cracking, but, in the present embodiment, the presence of cracking having the risk of leading to flaking can be precisely identified over the entire circumference of the tunnel lining surface 100.

When the image processing of the three dimensional image 120 of the tunnel lining surface 100 is performed, the technology of the infrared thermal imaging analysis device which belongs to the prior application of the applicant and is already patented (Japan Patent No. 5140892) may be applied for more precise analysis.

In this technology of the infrared thermal imaging analysis device, the information of temperature gradient overlapped in the infrared image is removed to display the image which further clarifies the difference between the sound portion and the damaged portion.

Performing the image processing by applying the technology of the infrared thermal imaging analysis device to the three dimensional image 120 of the tunnel lining surface 100 enables the image which further clarifies the difference between the sound and flat portion and the portion 304a with uplift of no shorter than 1 mm which has the risk of leading to flaking on the tunnel lining surface 100 to be obtained. Therefore, the presence of cracking having the risk of leading to flaking can be further precisely identified over the entire circumference of the tunnel lining surface 100.

The invention claimed is:

1. A tunnel lining surface inspection system wherein, while a vehicle is traveling in a tunnel, a three dimensional shape of a surface of a tunnel lining surface is inspected by using a light section method using photography means and slit laser beam projecting means mounted in the vehicle, and is processed into an image used for inspecting the tunnel lining surface, the system comprising
 a plurality of slit laser beam projecting means for projecting a long slit laser beam along a circumferential direction of the tunnel lining surface to each area along a circumferential direction of the one side face in the both side faces of the tunnel lining surface to the direction vertical to the surface of the tunnel lining surface,
 a plurality of photography means for photographing from a direction different from a projecting direction of the plurality of slit laser lights the each area along the circumferential direction of the one side face in the both side faces of the tunnel lining surface by photographing the slit laser direction emitted to the surface of the tunnel lining surface from the oblique direction having the collimation line inclined to the surface of the tunnel lining surface, and
 a fan-shaped member having predetermined width in a traveling direction of the vehicle, where its section vertical in a traveling direction of the vehicle with a fan shape forms an arc-shaped surface, being arranged in the vehicle so that one side face in both side faces of the tunnel lining surface corresponds to the arc-shaped surface of the fan-shaped member,
 wherein, the plurality of slit laser beam projecting means have the arc-shaped surface of the fan-shaped member as the arrangement surface, being installed, along the circumferential direction of the arc-shaped surface, and the plurality of photography means correspond to the each of the plurality of slit laser beam projecting means, and have the arc-shaped surface of the fan-shaped member as the arrangement surface, being installed along the circumferential direction of the arc-shaped surface, apart from a position where the slit laser beam positioning means are arranged by a predetermined distance in a vehicle traveling direction, and
 the system further comprises
 fixing and reversing means comprising drive axis which is the vertical center axis and a stage fixed to the frame of the vehicle, for fixing the fan-shaped member to a first measurement position where a three dimensional shape of the one side face in the both side faces of the tunnel lining surface can be measured, and 180° reversing the fan-shaped member around a vertical center axis to fix the fan-shaped member to a second measurement position where the three dimensional shape of the other side face in the both side faces of the tunnel lining surface can be measured, and
 image processing means for performing image processing to obtain the image used for inspecting the tunnel lining surface, by using a result of the three dimensional shape measurement of the one side face of the tunnel lining surface, measured in a state where the fan-shaped member is fixed to the first measurement position and a result of the three dimensional shape measurement of the other side face of the tunnel lining surface, measured in a state where the fan-shaped member is fixed to the second measurement position.

2. A vehicle used in a tunnel lining surface inspection system wherein, while a vehicle is traveling in a tunnel, a three dimensional shape of a surface of a tunnel lining surface is inspected by using a light section method using photography means and slit laser beam projecting means mounted in the vehicle, and is processed into an image used for inspecting the tunnel lining surface, the system comprising
 a plurality of slit laser beam projecting means for projecting a long slit laser beam along a circumferential direction of the tunnel lining surface to each area along a circumferential direction of the one side face in the both side faces of the tunnel lining surface to the direction vertical to the surface of the tunnel lining surface,
 a plurality of photography means for photographing from a direction different from a projecting direction of the plurality of slit laser lights the each area along the circumferential direction of the one side face in the both side faces of the tunnel lining surface by photographying the slit laser direction emitted to the surface of the tunnel lining surface from the oblique direction having the collimation line inclined to the surface of the tunnel lining surface, and
 a fan-shaped member having predetermined width in a traveling direction of the vehicle, where its section vertical in a traveling direction of the vehicle with a fan shape forms an arc-shaped surface, being arranged in the vehicle so that one side face in both side faces of the tunnel lining surface corresponds to the arc-shaped surface of the fan-shaped member,
 wherein, the plurality of slit laser beam projecting means have the arc-shaped surface of the fan-shaped member as the arrangement surface, being installed, along the circumferential direction of the arc-shaped surface, and the plurality of photography means correspond to each of the plurality of slit laser beam projecting means, and have the arc-shaped surface of the fan-shaped member as the arrangement surface, being installed along the circumferential direction of the arc-shaped surface, apart from a position where the slit laser beam positioning means are arranged by a predetermined distance in a vehicle traveling direction, and
 the system further comprises
 fixing and reversing means comprising drive axis which is the vertical center axis and a stage fixed to the frame of the vehicle, for fixing the fan-shaped member to a first measurement position where a three dimensional shape of the one side face in the both side faces of the tunnel lining surface can be measured, and 180° reversing the fan-shaped member around a vertical center axis to fix the fan-shaped member to a second measurement position where the three dimensional shape of the other side face in the both side faces of the tunnel lining surface can be measured.

3. The tunnel lining surface inspection system claimed in claim 1, wherein the plurality of slit laser beam projecting means and the plurality of photography means are characterized in that they have the arc-shaped surface of the fan-shaped member as the arrangement surface, being installed in zigzag along the circumferential direction of the arc-shaped surface.

4. The vehicle used in the tunnel lining surface inspection system, claimed in claim 2, wherein the plurality of slit laser beam projecting means and the plurality of photography means are characterized in that they have the arc-shaped surface of the fan-shaped member as the arrangement surface, being installed in zigzag along the circumferential direction of the arc-shaped surface.

\* \* \* \* \*